US00PP17161P3

(12) United States Plant Patent
Woody

(10) Patent No.: US PP17,161 P3
(45) Date of Patent: Oct. 24, 2006

(54) EASTERN REDBUD TREE NAMED 'ACE OF HEARTS'

(50) Latin Name: *Cercis canadensis L.*
Varietal Denomination: Ace of Hearts

(75) Inventor: Paul Buddy Ewing Woody, Morganton, NC (US)

(73) Assignee: Paul B. E. Woody, Morganton, NC (US)

( * ) Notice: Subject to any disclaimer, the term of this patent is extended or adjusted under 35 U.S.C. 154(b) by 382 days.

(21) Appl. No.: 10/744,404

(22) Filed: Dec. 23, 2003

(65) Prior Publication Data

US 2005/0138705 P1 Jun. 23, 2005

(51) Int. Cl.
*A01H 5/00* (2006.01)

(52) U.S. Cl. ..... Plt./216

(58) Field of Classification Search ..... Plt./216
See application file for complete search history.

(56) References Cited

PUBLICATIONS

Declaration of Paul Buddy Ewing Woody under 37 C.F.R. Section 1.132; Aug. 9, 2004.

*Primary Examiner*—Anne Marie Grunberg
*Assistant Examiner*—Annette H Para
(74) *Attorney, Agent, or Firm*—Myers Bigel Sibley & Sajovec, P.A.

(57) ABSTRACT

A new and distinct ornamental cultivar of *Cercis canadensis* called 'Ace of Hearts' is described that is a dwarf, compact tree with small, semi-glossy, heart-shaped leaves and a dense, dome-shaped canopy.

2 Drawing Sheets

Latin name of the genus and species: The Latin name of the novel cultivar disclosed herein is *Cercis canadensis* L. (Leguminosae Juss.).

Variety denomination: The inventive cultivar of eastern redbud tree disclosed herein has been given the cultivar denomination 'Ace of Hearts'.

BACKGROUND OF THE INVENTION

The redbud tree, *Cercis canadensis,* sometimes referred to as the Judas tree because it dates back to biblical times, is a small deciduous tree that displays an abundance of purple blossoms in the spring. It has large heart-shaped leaves during the summer, and may have long seedpods and yellow leaves in the fall. Redbed trees are generally used for ornamental purposes.

The inventive cultivar named 'Ace of Hearts' was discovered in a cultivated area of 300–400 *Cercis Canadensis* L. (Leguminosae Juss.) seedlings planted in 1997. The *C. Canadensis* seedlings were produced from seed. At the time of planting, the seedlings ranged in size from 18–24 inches (45–60 cm) in height and grew to 8–10 feet (around 3 meters) by the year 2000. The parents of seedlings in the mass planting, including those of the cultivar named 'Ace of Hearts' are unknown. 'Ace of Hearts' was selected in 2000 for its distinctive dwarf, compact habit; small, semi-glossy, heart-shaped leaves; and dense, dome-shaped canopy. While other redbud trees require some selective pruning to obtain a desirable shape, 'Ace of Hearts' requires no pruning to maintain its dense, domed shape.

SUMMARY OF THE INVENTION

'Ace of Hearts' is a new and distinct cultivar of eastern redbud tree characterized by its dwarf, compact habit, dome-shaped canopy and small, semi-glossy, heart-shaped leaves.

Like *C. canadensis* subsp. *mexicana* (Rose) Murray, 'Ace of Hearts' has small, shiny leaves; however, 'Ace of Hearts' is distinctive by lacking the wavy margins characteristic of *C. canadensis* subsp. *mexicana* (Rose) Murray. Further, 'Ace of Hearts' has smaller leaves than either *C. canadensis* subsp. *texensis* or *C. canadensis* subsp. *canadensis.* Moreover, 'Ace of Hearts' has green leaves unlike the intense red-purple leaves of the well-known cultivar 'Forest Pansy' (unpatented) and lacks the weeping growth form of 'Covey' (U.S. Plant Pat. No. 10,328) and 'Traveller', (U.S. Plant Pat. No. 8,640).

BRIEF DESCRIPTION OF THE DRAWINGS

The accompanying photographs are taken of a typical 7-year old 'Ace of Hearts' tree.

DETAILED BOTANICAL DESCRIPTION OF THE VARIETY

The following is a detailed botanical description of a new and distinct cultivar of *Cercis canadensis* known as 'Ace of Hearts'. Plant growth observations were of mature plants (approximately seven-years old) grown in full sun in field plots (soil pH of 6.5) in Burke County, N.C. Where dimensions, sizes, colors and other characteristics are given, it is to be understood that such characteristics are set forth as accurately as practicable. Those skilled in the art will appreciate that certain characteristics will vary with older or, conversely, with younger plants. 'Ace of Hearts' has not been observed under all possible environmental conditions. The phenotype of the cultivar may differ from the descriptions herein with variations in the environment such as season, temperature, light intensity, day length, cultural conditions, and the like. Color notations are based on The Royal Horticultural Society Colour Chart, The Royal Horticultural Society, London, 1995 edition.

Market Class

The market class of the cultivar is ornamental tree.

Parentage

The 'Ace of Hearts' cultivar was selected from a mass planting of *Cercis canadensis* L. (Leguminosae Juss.) at Morganton, N.C. The single, individual plant, now known as 'Ace of Hearts', was selected in 2000 because of its multitude of exceptional features, and has been propagated asexually since that time.

Asexual Reproduction

In August 2000, 'Ace of Hearts' was propagated asexually by budding at the Shadow Nursery in Winchester, Tenn. to produce three second-generation plants. Since that time, 'Ace of Hearts' has been asexually reproduced at the Shadow Nursery, predominantly by budding of seedlings, to increase the plant population and evaluate the stability and uniformity of the distinctive characteristics over several generations. Budding in August 2001 generated approximately 70, third generation plants and approximately 170 plants were produced in an August 2002 fourth generation. Asexual propagation of the new cultivar has shown that the unique features of this new eastern redbud tree are stable and the plant reproduces true to type in successive cycles of asexual propagation.

Technical Description of the Variety

Figure 1:
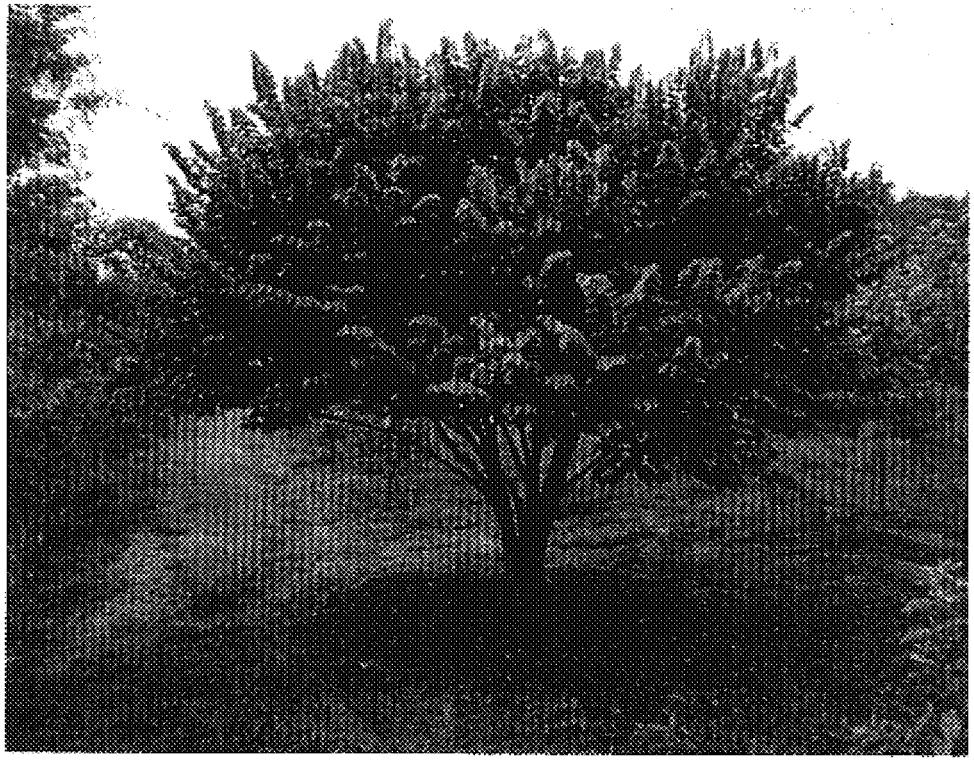
FIG. 1 shows a typical plant of 'Ace of Hearts' in the summer.

Plant habit: 'Ace of Hearts' has an average height of 12 feet (~4 meters) and an average spread of 15 feet (~5 meters). This cultivar has a dense crown and broad, dome-shaped canopy (FIG. 1).

*Trunk dimensions and appearance.*—'Ace of Hearts' has one trunk averaging 11 cm in diameter and 30 cm in height. The color of the bark of the trunk is grayish (RHS 197A).

*Branches from trunk.*—In general, five branches emerge from the trunk and are strongly ascending, divergent and 3–6 cm in diameter. The color of the bark of the mature branches is grayish (RHS 197B).

*Young branches.*—Slender, weakly flexuous, 2–4 mm diameter; the color of the bark of the youngest branches produced during the current season's growth is greenish, ranging between and including RHS 146B and RHS 146C; the bark of the branches produced during the prior season's growth is dark gray-brown to gray-brown (RHS 199A, 200B–C); bark becoming striated; inner wood is whitish, pith is solid.

*Lenticels.*—Numerous, prominent, weakly raised, orbicular to weakly oval in length, slightly longer than wide, about 0.1 to 0.4 mm in diameter, yellowish-green (152D) in color.

Figure 2:
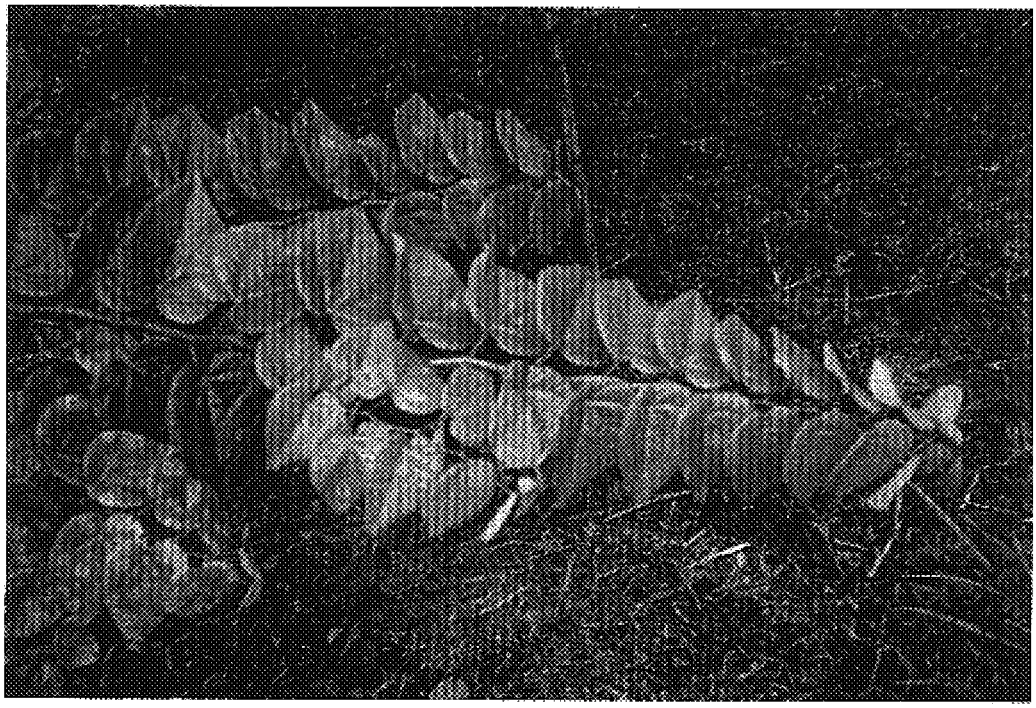
FIG. 2 shows leaves typical of 'Ace of Hearts'.

Foliage: Deciduous leaves are alternate, simple, broad, and ovate-cordate. In general, the leaves are (3) 4–6.5 cm in length and (3) 4–6.3 cm in width (FIG. 2). Margin: entire; apex: tapering to an acute or infrequently subacuminate, mucronate; base: cordate, lobes 7–15 mm long below petiole insertion, 10–17 mm wide between lobe bases; adaxial (upper) surface: dark green (individual leaves were RHS 132A, 136A, or 139A), smooth textured, somewhat glossy; abaxial (lower) surface: pale, grayish-green (RHS 191A), primary veins seven, palmate, veinlets conspicuously reticulate below with the naked eye, prominent at 10× magnification.

*Petioles.*—Slender, smooth, 2–2.5 cm long, 1–1.5 mm diameter, yellowish-green in color, ranging between and including 143C and 144B, becoming reddish-tinged (178A) on the adaxial surface when exposed to sun, bearing a 2–3 mm pulvinus distally.

*Pulvinus.*—Apically on the pedicel, 2–3 mm long.

Buds: Erect, inverted conical, 2–3 mm long, about 1–1.4 mm wide basally expanding to 2.4–3.5 mm wide apically; swelling in late March, reddish-purple (RHS 61A) in clusters of (2) 4–8.

*Bracts.*—Scale-like, imbricated, appressed, flabellate, obtuse, ciliolate, about 0.6–1.0 mm long and 1–1.5 mm wide.

*Pedicels.*—Less than ~1 mm in length.

*Calyx.*—Narrow campanulate; tube: ~2 mm long, ~1.5 mm wide; teeth: broad ovate, obtuse, ~0.5 mm long, ~1 mm wide.

Figure 3:
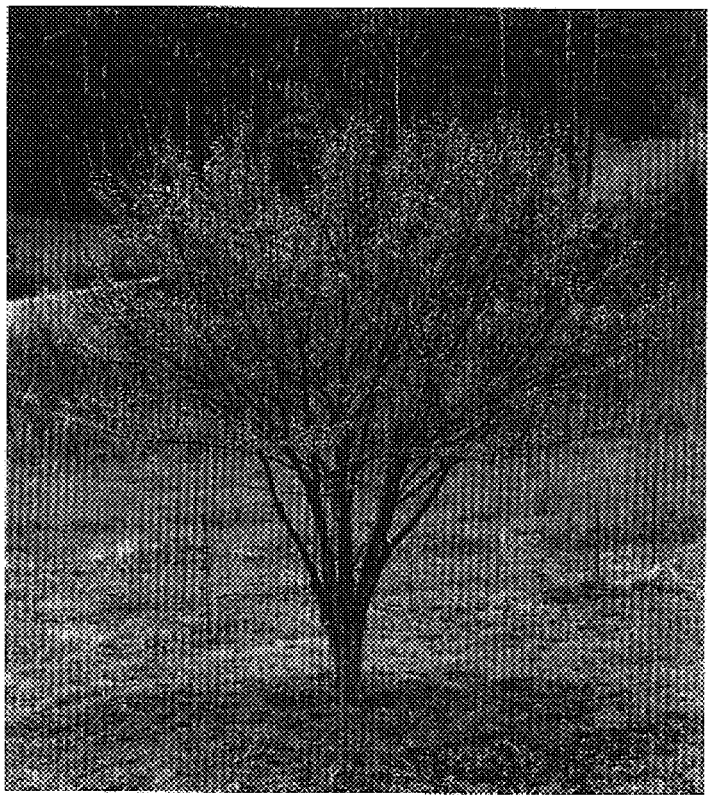
FIG. 3 shows a typical plant of 'Ace of Hearts' in the spring.

Inflorescence: Abundant, cauliflorous on old wood before leaves appear, bearing cluster of 2–6 flowers in early April (FIG. 3).

*Bracts.*—Imbricate, becoming larger distally, broad ovate, obtuse, ciliolate, 0.8–1.5 mm long, 0.6–1.3 mm wide.

*Pedicels.*—4–5 mm long in flower.

Figure 4:
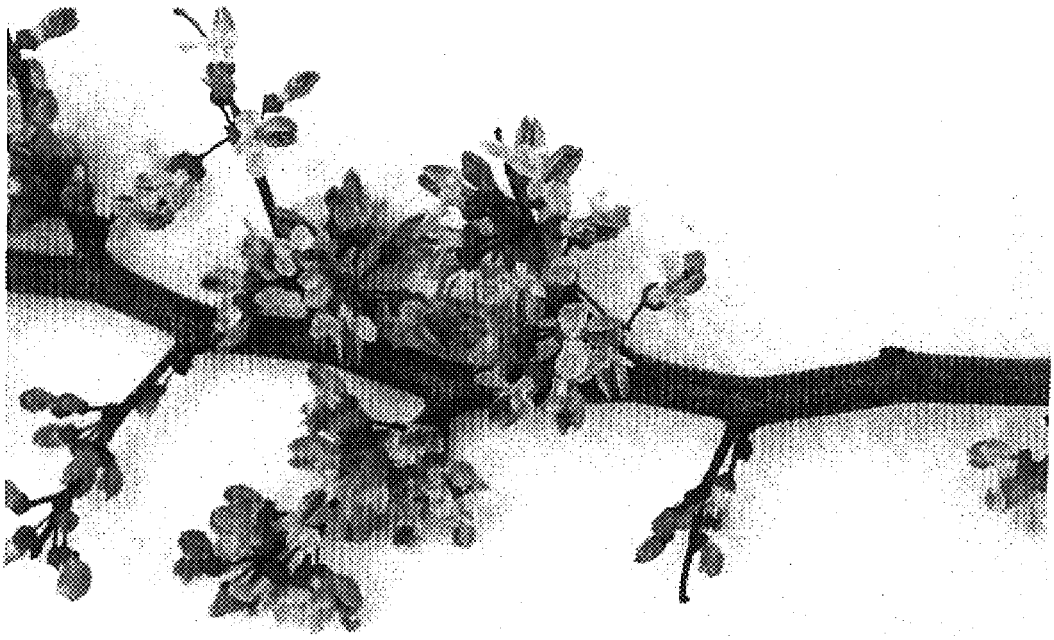
FIG. 4 shows flowers produced by 'Ace of Hearts'.

Flowers: Papilionaceous (pea-like), pedicillate, light violet (RHS 82A–B) (FIG. 4).

*Calyx.*—Broad campanulate, red-purple (RHS 71B–C); tube: 10-veined, ~1 mm long, ~3 mm wide; lobes: broad ovate, obtuse, 1–2 mm long, 1–1.5 mm wide, shriveling upon maturation.

*Petals.*—Five, papilionaceous, claws lacking pigmentation; two keel petals, enclosing reproductive organs, blade ~5 mm long, ~3 mm wide, claw ~2 mm; two wing petals, ascending, blade oblong, ~3 mm long, ~2 mm wide, claw ~2.2–2.5 mm; one banner petal, ~4 mm long, ~3 mm wide, claw ~2 mm.

*Stamens.*—Ten, distinct, free; filaments; ~4 mm long; anthers: ~0.5 mm.

*Pistil.*—One, exceeding stamens slightly; ovary: ~3.5 mm long; style: 1.8–2.0 mm long, curving some apically; stigma: capitate, ~0.3 mm diameter.

Fruit: Fruit is rarely produced. When produced, the fruit is a flattened legume, the fruiting pedicel is 12 mm, valves two, oblong, elongate-cuneate basally, apically acute, costate, 60 mm long, 14 mm wide, blackish-brown in color, ranging between and including RHS 200B to RHS 200C, costa (wing) is about 1 mm from the margin, beak is 1 mm long.

Seeds: Absent.

Hardiness: 'Ace of Hearts' is hardy, surviving temperatures below −3° C. The cultivar has performed well under extreme environmental conditions including cold, snow, ice storm, drought and heavy rains.

Comparison with Other *Cercis canadensis* subspecies and cultivars

'Ace of Hearts' is distinctive from the three subspecies of *Cercis canadensis,* (i.e., *canadensis, mexicana,* and *texenis*) which are distinguished primarily by native population ranges. *C. Canadensis* subsp. *mexicana* (Rose) Murray is characterized as having small, shiny leaves with wavy margins (Dirr (1998) In: Manual of Woody Landscape Plants. 5$^{th}$ Edition, Stipes Publishing Co., Champaign, Ill., pp 208–211), whereas 'Ace of Hearts' has a similar leaf size but lacks wavy margins. Of five herbarium species of *C. canadensis* subsp. *mexicana* located at the North Carolina State University Herbarium, two specimens (Russell 2184 and 2191) are similar in leaf size to 'Ace of Hearts' and the remaining three (Russell 2170, 2171 and 2183) have leaves that are larger than 'Ace of Hearts'. Subspecies *canadensis* and *texenis* generally have larger leaves than 'Ace of Hearts'.

In a comparison with known cultivars of *C. canadensis,* the leaves of 'Ace of Hearts' are green and lack the intense reddish-purple pigmentation and subdued reddish-purple hue common to 'Forest Pansy' in emerging and older leaves, respectively. Further, 'Covey' and 'Traveller' are dwarf in stature (up to 2 meters in height) and have arching-recurving branches which produce a weeping growth form, whereas 'Ace of Hearts' has a dense, dome-shaped canopy.

Likewise, in comparison to the other plants in the mass planting in which 'Ace of Hearts' was discovered, 'Ace of Hearts' is quite distinct (Table 1).

TABLE 1

| Characteristic | other Plants in Mass Planting | 'Ace of Hearts' |
|---|---|---|
| Size | About 18–25 ft × 21–26 ft | About 12 × 15 ft |
| Canopy | Spreading, open to obtuse | Compact, dome-shaped |
| Leaf Size | 7.5–13 cm × 8–15 cm | 4–6.5 cm × 3–6 cm |
| Fruits | Abundant, persistent | Rare to absent |

Herbarium Vouchers

Herbarium vouchers will be deposited upon patenting at North Carolina State University Herbarium, Raleigh, N.C. and The National Arboretum, Washington, D.C. with Holotype: *Fantz* & *Woody* 7401 (foliage) and Paratypes: *Fantz* & *Woody* 7290 (flowers) and *Fantz* & *Woody* 7265 (buds).

What is claimed is:

1. A new and distinct cultivar of *Cercis canadensis* plant named 'Ace of Hearts', substantially as illustrated and described herein.

* * * * *